US008324441B2

(12) United States Patent
Wegerer et al.

(10) Patent No.: US 8,324,441 B2
(45) Date of Patent: Dec. 4, 2012

(54) PENTANE CATALYTIC CRACKING PROCESS

(75) Inventors: David A. Wegerer, Lisle, IL (US);
Stephen M. Casey, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 782 days.

(21) Appl. No.: 11/872,776

(22) Filed: Oct. 16, 2007

(65) Prior Publication Data

US 2009/0099398 A1    Apr. 16, 2009

(51) Int. Cl.
*C07C 4/02* (2006.01)
*C07C 5/22* (2006.01)

(52) U.S. Cl. ......... 585/648; 585/324; 585/650; 585/752

(58) Field of Classification Search .................. 585/312, 585/313, 322, 525, 660, 664, 670, 671; 502/202, 502/207, 223; 422/192
See application file for complete search history.

(56) References Cited

U.S. PATENT DOCUMENTS

| | | | | |
|---|---|---|---|---|
| 3,558,523 A * | 1/1971 | Rausch | ......................... | 502/223 |
| 3,647,682 A * | 3/1972 | Rabo et al. | ............... | 208/120.15 |
| 4,433,190 A * | 2/1984 | Sikkenga et al. | ............. | 585/660 |
| 4,567,023 A * | 1/1986 | Greenwood et al. | .......... | 422/192 |
| 5,043,522 A * | 8/1991 | Leyshon et al. | ............... | 585/651 |
| 6,197,717 B1 * | 3/2001 | Alexander et al. | ............ | 502/207 |
| 6,713,658 B1 | 3/2004 | Dath et al. | ..................... | 585/653 |
| 6,768,037 B2 | 7/2004 | O'Rear et al. | ................ | 585/651 |
| 6,867,341 B1 | 3/2005 | Abrevaya et al. | ............. | 585/650 |
| 6,977,321 B1 | 12/2005 | Dath et al. | ..................... | 585/653 |
| 7,128,827 B2 | 10/2006 | Tallman et al. | .................. | 208/78 |
| 7,875,755 B2 * | 1/2011 | Voskoboynikov | ............ | 585/324 |
| 2003/0220530 A1 | 11/2003 | Boelt et al. | ..................... | 585/648 |

OTHER PUBLICATIONS

Magee et al, Editors, Fluid Catalytic Cracking: Science and Technology, Elsevier, 1993, p. 505.*
Brenner, Annette M., et al.; "Hydrogen production in the conversion of 2-methylbutane over a series of acid catalysts" Catalysis Today 44 (1998) pp. 235-244.
Kissin, Yury V.; "Chemical Mechanism of Hydrocarbon Cracking over Solid Acidic Catalysts" Journal of Catalysis 163, (1996) pp. 50-62.
Yaluris, G., et al.; "2-Methylhexane Cracking on Y Zeolites: Catalytic Cycles and Reaction Selectivity" Journal of Catalysis 165 (1997) pp. 205-220.

* cited by examiner

*Primary Examiner* — Tam M Nguyen
(74) *Attorney, Agent, or Firm* — Arthur E Gooding

(57) ABSTRACT

A process is presented for the production of light olefins from a paraffin stream comprising pentanes. The process includes a series of pentane cracking reactors where a process stream having pentane in the process stream passes through the reactors with the process stream heated between each pair of successive reactors, and where the process is operated at low pressures.

22 Claims, 1 Drawing Sheet

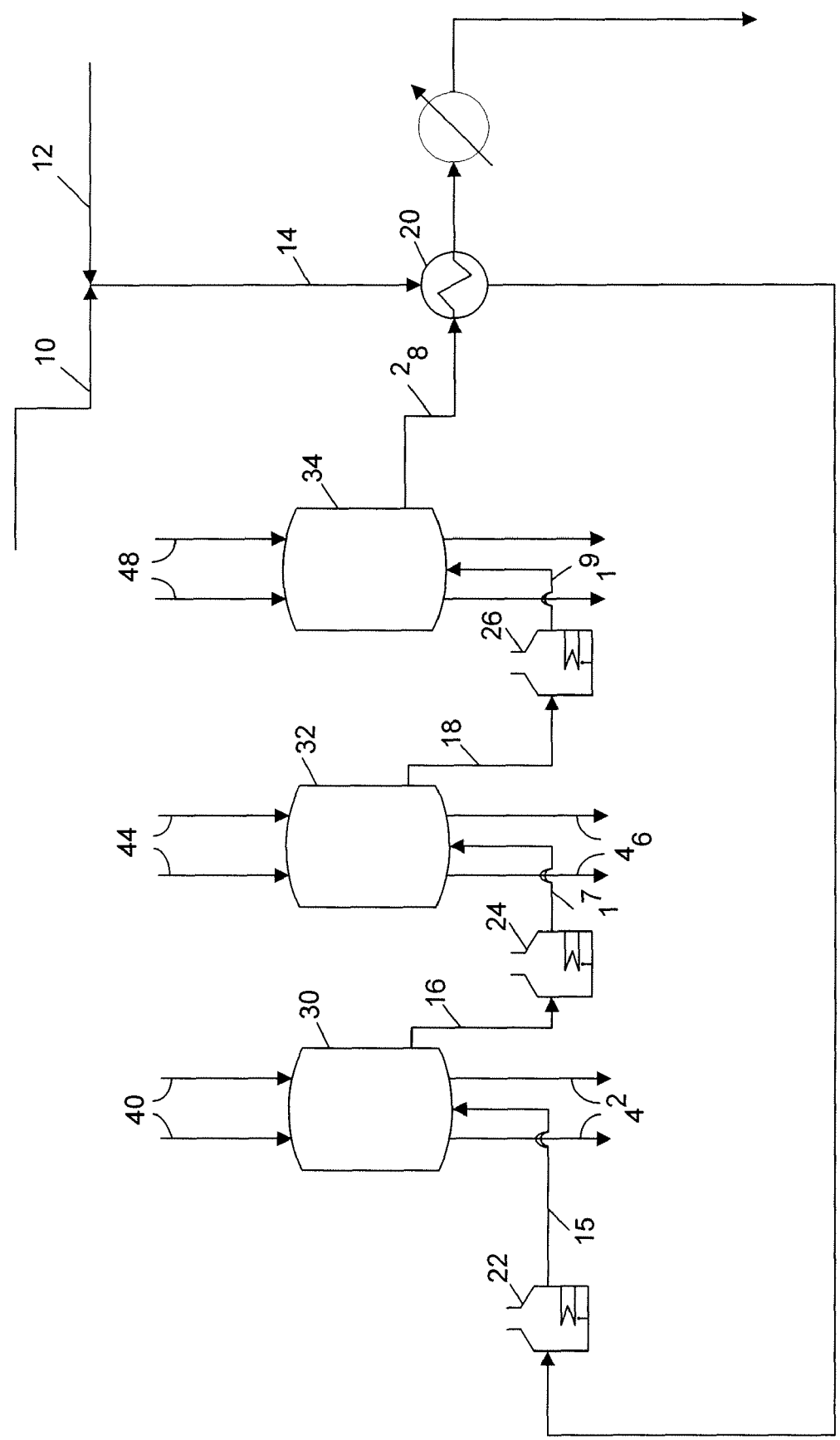

PENTANE CATALYTIC CRACKING PROCESS

BACKGROUND OF THE INVENTION

This invention relates to the production of light olefins by the cracking of larger paraffins. In particular, the conversion of pentanes to light olefins.

Gasoline, or motor fuel, comprises a blend of many hydrocarbon compounds to achieve desirable properties relating to combustion. Fuel quality demands and tightening automotive emission standards have led to changes in gasoline formulation. Requirements for the reformulated gasoline include lower vapor pressure, lower final boiling point, increased oxygenate content, and lower content of olefins and aromatics. Motor fuels have included significant quantities of isopentane because of its high octane value, and because isopentane is one of the most volatile components in a motor fuel, it contributes to the ability to start a cold engine.

One environmental concern has been the evaporation of hydrocarbons, and these concerns have led to a reduction in the Reid vapor pressure (RVP) specification of motor fuels. Due to these increased environmental concerns and regulations, isopentane has become a component that is less favored as a fuel blending component. The removal of pentane and isopentane from motor fuels allows for redirection of these hydrocarbon components to more profitable uses of the pentanes.

SUMMARY OF THE INVENTION

The present invention is a process for generating light olefins of ethylene and propylene from a paraffinic feedstream comprising hydrocarbons having from 4 to 6 carbon atoms. The feedstream is passed through a plurality of reactors in series with each successive reactor cracking a portion of the hydrocarbon stream to light olefins. The feedstream as it passes between reactors is heated to a reactor inlet temperature by either a heat exchanger or fired heater. The reactors comprise a catalyst for cracking pentane to light olefins and are operated at pressures below 450 kPa (65 psia).

Other objects, advantages and applications of the present invention will become apparent to those skilled in the art from the following detailed description and drawing.

BRIEF DESCRIPTION OF THE DRAWING

The FIGURE is a flow scheme of an embodiment of the present invention.

DETAILED DESCRIPTION OF THE INVENTION

Isopentane and pentane have become less favored as a fuel blending component, and need to be redirected to a more beneficial use of these compounds. The need for more light olefins, ethylene and propylene, provide a useful redirection of the pentane compounds. Catalytic cracking of pentane converts pentanes, and preferably isopentane to higher valued ethylene and propylene.

A new process is presented that converts paraffins to light olefins. A feedstream comprising paraffins having from 4 to 6 carbon atoms is recovered and directed to a plurality of pentane cracking reactors to convert the paraffins to light olefins comprising ethylene and propylene. The process as shown in the FIGURE, comprises one embodiment of the present invention. A fresh feedstream 10 is mixed with a recycle feed 12 to form a combined feed 14. The combined feed 14 is preheated in a first heat exchanger 20 with heat from a product stream 28. The combined feed 14 is further heated with a second heat exchanger 22 to raise the first feed inlet temperature to between 500° C. and 650° C. The heated combined feed 15 reacts in the first reactor 30 to generate a first intermediate stream 16. The first intermediate stream 16 is heated in a third heat exchange 24 generating a heated first intermediate stream 17 to a second feed inlet temperature between 570° C. and 630° C. The heated first intermediate stream 17 is passed to a second reactor 32 to generate a second intermediate stream 18. The second intermediate stream 18 is heated in a fourth heat exchanger 26 generating a heated second intermediate stream 19 to a third feed inlet temperature between 570° C. and 630° C. The heated second intermediate stream 19 is passed to a third reactor 34 to generate a product stream 28. The product stream 28 comprises light olefins of ethylene and propylene. The reactors are preferably operated at temperatures between 500° C. and 650° C., and at pressures less than 450 kPa (65 psia). More preferably, the reactors are operated at pressures between 100 kPa (14.5 psia) and 300 kPa (43.5 psia). In this embodiment, the reactors 30, 32, and 34 are radial flow reactors.

In this embodiment, the first reactor 30 receives regenerated catalyst from a catalyst regeneration system. The regenerated catalyst 40 passes through the first reactor 30 wherein the heated feedstream 15 reacts. The catalyst leaves the first reactor 30 through a catalyst outlet 42 and is directed to a catalyst inlet 44 for the second reactor 32. The catalyst passes through the second reactor 32 wherein the heated first intermediate stream 17 reacts. The catalyst leaves the second reactor 32 through the second reactor catalyst outlet 46 and is directed to a catalyst inlet 48 for the third reactor 34. The catalyst passes through the third reactor 34 wherein the heated second intermediate stream 19 reacts.

Following the last reactor in any number of reactors for this invention, the catalyst is passed to a regeneration zone, where the catalyst is regenerated and then returned to the first reactor.

The reaction conditions of this process further comprises controlling the ratio of fresh paraffin feedstream to recycle paraffin feedstream, and the flow of the feedstream through the reactor, or the weight hourly space velocity (WHSV). In one embodiment the ratio of combined feedstream to fresh paraffin feedstream is between 1.1:1 and 10:1, and preferably the combined feedstream to fresh paraffin feedstream ratio is between 1.2:1 and 4:1. In one embodiment, the WHSV is between 1 and 20 $hr^{-1}$, and preferably the WHSV is between 2 and 10 $hr^{-1}$.

In another embodiment, the process further comprises separating the product stream 28 into a light olefin stream comprising ethylene and propylene, and a recycle stream comprising C4, C5 hydrocarbons that are directed to the pentane cracking reactors, and preferably to the first pentane cracking reactor. The C4, C5 hydrocarbons can be predominantly paraffins and olefins, with aromatics being removed during the process.

The process was simulated and compared to typical pentane cracking processes as now practiced in the industry. The results are shown in Table 1, where the amounts are shown in weight percents in the product streams. Typical pentane cracking yields a low portion of the pentanes cracked to ethylene and propylene. The present process consumes a significantly higher portion and doubles the amount of ethylene and propylene generated over the currently as practiced process.

TABLE 1 product yields

| | Typical Isopentane cracking yields |
|---|---|
| H2, methane, ethane | 8 |
| Ethylene | 7 |
| Propane | 2 |
| Propylene | 13 |
| Mixed C4s | 12 |
| Isopentane | 50 |
| Other C5s | 3 |
| C6 plus | 5 |

In another embodiment, the process further comprises the use of a paraffin isomerization reactor. Isoparaffins are more selectively catalytically cracked to produce more light olefins than normal paraffins, and the product stream from isoparaffin cracking will contain a relatively greater amount of light olefins. The cracking of isoparaffins, specifically isopentane, will more selectively generate ethylene and propylene, whereas, the cracking of paraffins will, in general, generate a light olefin and a paraffin that requires further processing. The product stream 28 from the last reactor is passed to a separation section, thereby generating a light olefin product stream and a paraffin rich stream. The light olefin product stream will comprise predominantly ethylene and propylene. The paraffin rich stream will comprises unreacted paraffins in the C4 to C6 range, and some lighter paraffins such as propane and ethane. Additional components are also generated, such as methane, which can be separated out and redirected to other process units. The paraffin rich stream is passed through an isomerization reactor to increase the isoparaffin content in the paraffin rich stream. The isomerized paraffin stream is passed to the pentane cracking reactors.

In yet another embodiment, the process comprises using a plurality of fixed bed reactors, wherein at least one of the fixed bed reactors is off-line for regeneration of the catalyst. This creates a cyclic process for continuous cracking of the pentane stream and continuous generation of a product stream. The process includes passing a feedstream comprising pentane through a plurality of on-line pentane cracking reactors in series, where the feedstream passes through a first reactor, thereby generating a first intermediate stream. The first intermediate stream passes through a second reactor thereby generating a second intermediate stream, and the intermediate streams continue passing sequentially through the reactors to the last reactor to generate a product stream comprising light olefins. The intermediate streams are heated with a heating unit to raise the intermediate stream's temperature to a reactor inlet temperature. The reactors are operated at reaction conditions that include operating at pressures below 450 kPa (65 psia).

The reactors each comprise a fixed bed catalyst for cracking pentane, and the process has at least one of the reactors off-line where the catalyst in the off-line reactors is regenerated at regeneration conditions. The operation of the reactors is such that as one reactor is taken off-line, one of the off-line reactors is brought back into service and put on-line.

The product stream is passed to a separation process for recovering the light olefins, ethylene and propylene. Methods of separation are known in the art, and are and not detailed here.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for producing light olefins from pentane comprising:

passing a feedstream comprising pentane through a plurality of pentane cracking reactors with each reactor containing a catalyst, comprising a first reactor and a last reactor, in series with heaters disposed between successive reactors, thereby generating an effluent stream comprising light olefins, where the feedstream enters a first reactor and the first reactor generates an intermediate stream, the intermediate stream is heated and passed to a subsequent reactor, and where each subsequent reactor generates an intermediate stream that is heated and passed to the next subsequent reactor, and wherein the last reactor generates a product stream comprising light olefins, wherein the isopentane is more selectively cracked than n-pentane;

passing the catalyst sequentially through the reactors, where each reactor has a catalyst inlet and a catalyst outlet, and where the catalyst flows through a catalyst inlet through a reactor and out a catalyst outlet, and where the catalyst flowing out a catalyst outlet is passed to a subsequent reactor catalyst inlet;

wherein the reactors comprise a catalyst for cracking the pentane feedstream to light olefins and the reactors are operated at a pressure below 450 kPa; and passing the product stream to a separation unit, thereby generating a light olefin product stream and an n-pentane rich stream;

passing the n-pentane rich stream through an isomerization reactor to increase the isopentane content of the n-pentane rich stream; and passing the isomerized n-pentane rich stream to the pentane cracking reactors, thereby generating an increased propylene content in the product stream.

2. The process of claim 1 further comprising passing the catalyst through a regeneration zone, wherein the flowing from the last reactor catalyst outlet is passed to the regeneration zone, and catalyst from the regeneration zone is passed to the first reactor catalyst inlet.

3. The process of claim 1 wherein the reactors comprises radial flow reactors.

4. The process of claim 1 wherein the pentane feed stream comprises paraffinic hydrocarbons in the C4 to C6 range.

5. The process of claim 1 wherein the light olefins comprise ethylene and propylene.

6. The process of claim 1 further comprising separating out C4 and higher hydrocarbons from the effluent stream and recycling the C4 and higher hydrocarbons to the pentane cracking reactors.

7. The process of claim 1 wherein the reaction conditions include a temperature between 500° C. and 650° C., and a pressure between 100 kPa and 300 kPa.

8. The process of claim 1 wherein the WHSV is between 1 and 20 $hr^{-1}$.

9. The process of claim 8 wherein the WHSV is between 2 and 10 $hr^{-1}$.

10. The process of claim 1 wherein the combined feed to fresh feed ratio is between 1.1:1 and 10:1.

11. The process of claim 10 wherein the combined feed to fresh feed ratio is between 1.2:1 and 4:1.

12. A process for producing light olefins from pentane comprising:
- passing a feedstream comprising pentane through a plurality of on-line pentane cracking reactors, comprising a first reactor and a last reactor, in series with heaters disposed between successive reactors, thereby generating an effluent stream comprising light olefins, where the feedstream enters a first reactor and the first reactor generates an intermediate stream, the intermediate stream is heated and passed to a subsequent reactor, and where each subsequent reactor generates an intermediate stream that is heated and passed to the next subsequent reactor, and wherein the last reactor generates a product stream comprising light olefins, wherein the isopentane is more selectively cracked than n-pentane;
- passing the product stream to a separation unit, thereby generating a light olefin product stream and an n-pentane rich stream;
- passing the n-pentane rich stream through an isomerization reactor to increase the isopentane content of the n-pentane rich stream; and
- passing the isomerized n-pentane rich stream to the pentane cracking reactors, thereby generating an increased propylene content in the product stream;
- wherein the reactors comprise a fixed bed catalyst for cracking the pentane feedstream to light olefins and the reactors are operated at a pressure below 450 kPa, and wherein there is at least one additional reactor that is off-line, and wherein the reactors are operated such that, periodically, the off-line reactor is brought on-line and one of the plurality of on-line reactors is taken off-line.

13. The process of claim 12 wherein the off-line reactor is being regenerated at regeneration conditions.

14. The process of claim 12 wherein the reactors comprise radial flow reactors.

15. The process of claim 12 wherein the pentane feed stream comprises paraffinic hydrocarbons in the C4 to C6 range.

16. The process of claim 12 wherein the light olefins comprise ethylene and propylene.

17. The process of claim 12 further comprising separating out C4 and higher paraffins and olefins from the effluent stream and recycling the C4 and higher paraffins and olefins to the pentane cracking reactors.

18. The process of claim 12 wherein the reaction conditions include a temperature between 570C and 630C, and a pressure between 100 kPa and 450 kPa.

19. The process of claim 12 wherein the WHSV is between 1 and 20 $hr^{-1}$.

20. The process of claim 19 wherein the WHSV is between 2 and 10 $hr^{-1}$.

21. The process of claim 12 wherein the combined fresh feed to recycle feed ratio is between 1.1:1 and 3:1.

22. The process of claim 21 wherein the combined fresh feed to recycle feed ratio is between 1.2:1 and 2:1.

* * * * *